(12) United States Patent
St.John et al.

(10) Patent No.: US 7,547,549 B2
(45) Date of Patent: Jun. 16, 2009

(54) METHOD TO PRODUCE A HYBRID CELL HAVING A SINGLE MITOCHONDRIAL GENOTYPE

(75) Inventors: Justin St.John, Droitwich Spa (GB); Keith Henry Stockman Campbell, West Bridgford (GB)

(73) Assignee: The University of Birmingham, Birmingham (GB)

( * ) Notice: Subject to any disclaimer, the term of this patent is extended or adjusted under 35 U.S.C. 154(b) by 220 days.

(21) Appl. No.: 10/501,354

(22) PCT Filed: Jan. 14, 2003

(86) PCT No.: PCT/GB03/00095

§ 371 (c)(1),
(2), (4) Date: Dec. 27, 2004

(87) PCT Pub. No.: WO03/057863

PCT Pub. Date: Jul. 17, 2003

(65) Prior Publication Data

US 2005/0120402 A1    Jun. 2, 2005

(30) Foreign Application Priority Data

Jan. 14, 2002  (GB) ................. 0200804.3

(51) Int. Cl.
*C12N 15/00* (2006.01)
*C12N 5/00* (2006.01)

(52) U.S. Cl. .......... 435/440; 435/325; 435/375

(58) Field of Classification Search ......... None
See application file for complete search history.

(56) References Cited

FOREIGN PATENT DOCUMENTS

WO    WO 01/30980 A2    5/2001
WO    WO 01/30980 A3    5/2001

OTHER PUBLICATIONS

Meirelles et al (2001) Complete Replacement of the Mitochondrial Genotype in a Bos indicus calf Reconstituted by Nuclear Transfer to a Bos taurus Oocyte. Genetics. May 2001, vol. 158, pp. 351-356.*
Levy et al. Transfer of Chloramphenicol-Resistant Mitochondrial DNA into the Chimeric Mouse. Transgenic Res. 1999, vol. 8, pp. 137-145.*
Sims et al. Production of Calves by Transfer to Nuclei from Cultured Inner Cell Mass Cells. Proc. Natl. Acad. Sci. Jun. 1993, vol. 990, pp. 6143-6147.*
Hiendleder et al. Transmitochondrial Differences and Varying Levels of Heteroplasmy in Nuclear Transfer Cloned Cattle. Molec. Reprod. Devel. 1999, vol. 54, pp. 24-31.*
Keith H.S. Campbell et al., Nuclear Transfer in Practice., Cloning and Stem Cells., 2001, vol. 3, No. 4, p. 201-208, United Kingdom.
Hiroshi Shitara et al., Selective and Continuous Elimination of Mitochondria Microinjected into Mouse Eggs from Spermatids, but not from Liver Cells, Occurs throughout Embryogenesis., Genetics, p. 1277-1284, Nov. 2000.
Jonathan Van Blerkom et al., Mitochondrial Transfer Between Oocytes; Potential Applications of Mitochondrial Donation and the Issue of Heteroplasmy, European Society for Human Reproduction and Embryology, p. 2857-2868, vol. 13 No. 10, Boulder, Co.
Albert S. Jun et al., Use of Transmitochondrial Cybids to Assign a Complex 1 Defect to the Mitochondrial DNA-Encoded NADH Dehydrogenase Subunit 6 Gene Mutation at Nucleotide Pair 14459 that Causes Leber Hereditary Optic Neuropathy and Dystonia. Mar. 1996, p. 771-777, American Society of Biology, Atlanta, GA.

* cited by examiner

*Primary Examiner*—Deborah Crouch
(74) *Attorney, Agent, or Firm*—Fulbright & Jaworski

(57) ABSTRACT

The present invention relates to a method of producing a viable hybrid cell having a single functional mitochondrial population. The method comprises the step of introducing genomic DNA from a mitochondrially depleted donor cell into a recipient cell from which genomic DNA has been removed.

4 Claims, No Drawings

METHOD TO PRODUCE A HYBRID CELL HAVING A SINGLE MITOCHONDRIAL GENOTYPE

The present invention relates in at least some of its aspects to methods of producing cells, and to improved cloning methods, as well as to cells and non-human animals produced by said methods.

The technique of nuclear transfer (NT) allows the production of offspring by the reconstruction of an oocyte, egg, zygote, or early embryo. Genetic material from a donor cell (sometimes referred to as a karyoplast) is transferred to a suitable recipient cell (sometimes referred to as a cytoplast) from which the nuclear or genomic genetic material has been removed. In the first demonstrations of this technique successful development was only obtained when the donor genetic material was taken from apparently undifferentiated cells or blastomeres from early embryos. Subsequently, donor genetic material from differentiated cells maintained in culture and isolated from embryonic (Campbell et al. Nature 380:64-66), foetal and adult tissues (Wilmut et al Nature 385: 810-813) has been successfully used. The aforementioned reports form the basis of patent applications WO 97/07669 and WO 97/07668 the contents of which are incorporated herein by reference. Subsequently, live offspring have been obtained utilising a range of cell types and techniques e.g. in mouse using cell populations derived directly ex vivo as nuclear donors (Wakayama et al., Nature 394:369-373) and from a range of cultured cell types including foetal fibroblasts. More recently live piglets were produced using a modified NT procedure (Polejaeva et al., Nature 407: 29-30, WO 00/22098). The contents of the aforementioned publication and patent application are incorporated herein by reference. The successful use of differentiated cells has now been demonstrated in sheep, cattle, goats, pigs and mice.

The use of nuclear transfer technology has many benefits and uses in the production of mammalian embryos foetuses and offspring. These include but are not limited to;
1. The ability to carry out precise genetic modification of cultured cells to be used as nuclear donors prior to embryo reconstruction. Such modifications include but are not limited to, random gene addition, addition of multiple copies of a transgene, addition of a transgene at a precise location (targeted addition or "knockin"), gene removal ("knockout"), gene inactivation by targeted insertion, gene replacement, and modification of any gene or its control sequences and gene multiplication.
2. The ability to carry out multiple genetic modifications in a single animal either by multiple genetic modifications of a cell population in culture or by sequential genetic modification, nuclear transfer and re-isolation of a cell population from the embryo, foetus or animal so produced.
3. The ability to increase the lifespan of cultured cell populations to be used for genetic modification by nuclear transfer and re-isolation of a cell population from the embryo, foetus, juvenile or adult animal so produced.
4. The ability to produce multiple copies of an animal from a genetically modified selected and cloned cell population.
5. The ability to produce multiple copies of any embryo, foetus, juvenile or adult animal by nuclear transfer from cells taken directly ex vivo, or cell populations derived from any tissues taken from any of these stages with or without culture in vitro.
6. The ability to store intact genomes for long periods (e.g. by freezing cell populations in liquid $N_2$) and to subsequently use these stored cells for the production of offspring by nuclear transfer.
7. The ability to dedifferentiate somatic nuclei and to produce undifferentiated cells that may be used for production of chimeric embryos, foetuses and adult animals by embryo aggregation or injection or to produce embryonic stem cell or embryonic germ cell populations.
8. The ability to dedifferentiate any somatic cell type by nuclear transfer and to isolate from the embryo so produced embryonic stem cells, germ cells or any other desired specialised or unspecialised cell type e.g. neurones.

Genetic modification of animals and the production of stem cell and differentiated cell populations by nuclear transfer technology have numerous uses in the fields of human medicine, agriculture, genetic preservation and research. These include but are not limited to the production of human therapeutic proteins in the bodily fluids, disease prevention, increasing required production traits, cell based therapies, cell based delivery systems for genetic therapy, and tissue and organ transplantation. The uses of such technology are discussed WO 98/30683 and WO 98/39416 which are included herein by reference.

In general, oocytes arrested at metaphase of the second meiotic division have been used as the recipient. The donor genetic material has been introduced into the recipient cell cytoplasm by the processes of cell fusion or injection of intact cells, lysed cells or nuclei. Transfer of genetic material may occur either at the time of activation, preceding activation (patent applications WO 97/07669 and WO 97/07668) or following activation (Campbell et al., Biol. Reprod. 49 933-942 (1993); Campbell et al Biol. Reprod. 50 1385-1393 (1994)). In each of these instances the ploidy of the reconstructed embryo must be maintained by the use of donor genetic material at an appropriate stage of the cell cycle (Campbell et al., Reviews of Reproduction 1:40-46, Campbell, K. H. S., Cloning 1:3-15). This process may be coupled with genetic manipulation techniques for the production of transgenic offspring (Schnieke et al., Science 278:2130-2133, McCreath et al., Nature 405: 1066-1069). The use of nuclear transfer coupled to genetic modification of cells in culture and their selection prior to animal production has a number of advantages including;
1. Production of non-mosaic animals ensuring germ line transmission of the genetic modification/s.
2. An increased efficiency in the production of such genetically modified animals.
3. The production of multiple copies of the offspring thereby reducing the generation interval to produce flocks or herds for production purposes or increasing the numbers of animals for dissemination of genetic modification into the population as a whole.
4. The production of animals containing multiple genetic modifications.
5. The production of transgenic animals with superior expression characteristics by utilisation of the pre-selection of the integration site of the transgene.

However, as well as genomic DNA, cells also contain extra-nuclear DNA such as that found in mitochondria. Mitochondria are the mammalian cell's major producer of energy, through their ability to generate adenosine 1,4,5-triphosphate (ATP). The vast majority qf a cell's ATP is generated by the Electron Transfer Chain (ETC) through the process of oxidative phosphorylation (OXPHOS), also known as cellular respiration. Each mitochondrion possesses one or more copies of a circular genome known as mitochondrial DNA (mtDNA). MtDNA encodes some of the genes necessary for ATP production through OXPHOS and mutation or deletion of these genes can lead to mitochondrial disease, which can be severely debilitating or lethal.

Normally in mammals and humans, mtDNA is inherited solely through the offspring's mother. Transmission of mtDNA to the offspring is thought to be restricted to a few molecules that pass through a genetic 'bottleneck', or restriction event, that is hypothesised to take place during very early oogenesis—the process that generates the female gametes during embryogenesis. However, offspring generated through interspecific crossing (crossing between two different strains) can inherit both paternal and maternal mtDNA.

According to a first aspect of the present invention there is provided a method of producing a viable hybrid cell having a single functional mitochondrial population, comprising the step of introducing genomic DNA from a mitochondrially depleted donor cell into a recipient cell from which genomic DNA has been removed.

As used herein a single functional mitochondrial population refers to a population of functional mitochondria derived from a single source (i.e. said mitochondrial population is substantially genetically identical), and cells produced using mitochondrially depleted cells will henceforth be referred to as cybrids. Strictly speaking, the term "mitochondrially depleted cell" ($mt^0$) relates to a cell having no mitochondria, whereas a mtDNA depleted cell ($mtDNA^0$) is a cell having non-functional mitochondria, i.e. mitochondria incapable of synthesising ATP by oxidative phosphorylation which may be due to damaged mtDNA or the complete absence of mtDNA. As used herein, however, reference to "mitochondrial depletion", or "mitochondrially depleted cells" may relate to the production of $mt^0$ or $mtDNA^0$ cells, unless the context requires otherwise.

Preferably, the recipient cell is arrested during DNA removal, in which case the method preferably includes a reactivation step after the genomic DNA has been removed from the recipient. Said reactivation step may be effected on the recipient cell (i.e. before introduction of genetic material from the donor cell) or on the hybrid cell (i.e. after introduction of genetic material from the donor cell).

Preferably, the recipient cell is an oocyte, a zygote, or a two-cell embryo. More preferably, the recipient is an oocyte. Said oocyte may be parthenogenetically activated, for example, through androgenesis and gynogenesis. Most preferably, the oocyte is arrested at metaphase of the second meiotic division when the genomic DNA is removed.

Also according to said first aspect there is provided a hybrid cell and an animal producible by said method.

It will be understood that either or both of said donor cell and recipient cell may be genetically modified, giving rise to a genetically modified hybrid cell or animal.

It is known that, in previously described cloning methods, cloned cells, although identical with regard to genomic DNA, will have inconsistent patterns of mitochondrial inheritance and often possess mixed mitochondrial populations (heteroplasmy) (Takeda et al., 1999, J Reprod Fertil; 116: 253-9. Hiendleder et al., 1999, Mol Reprod Dev, 54: 24-31. Steinborn et al., 1998a, FEBS Letts; 426: 352-356. Steinborn et al., 1998b, FEBS Letts; 426: 357-361). This heteroplasmy can result from the introduction of functional mitochondrial DNA (mtDNA) from both the donor and the recipient cells, and/or the use of recipient cells from different sources. Due to this heteroplasmy, cloned offspring produced by the previously described cloning methods will not be true clones. The use of these offspring having heteroplasmy for the study of genomic disorders and for drug screening may lead to significantly misleading data as more than one variable will have been introduced into the investigation resulting in similar parameters not being analysed. The understanding of the pathogenesis of mtDNA mutations and deletions has been enhanced by the use of immortalised, mtDNA depleted ($mtDNA^0$) cell lines and mitochondrially depleted cells ($mt^0$). MtDNA is eliminated or rendered non-functional through culturing with low concentrations of ethidium bromide, whilst mitochondria are eliminated through culturing with, for example, Rhodamine 6G. The $mtDNA^0$ cells are then maintained in an anaerobic media containing uridine, pyruvate and lactate to promote cell survival (see King & Attardi, 1996a, Meths Enzym; 264: 304-313). Once these cell lines have been established, they can then be repopulated with a source of mutant mtDNA, often isolated from a patient with a mtDNA disease. The mutant cells are enucleated (nucleus removed) and this population of cells is fused by either chemical, electrical or viral means with the $mtDNA^0$ cells to construct a functional cybrid. Following treatment with Rhodamine 6G, $mt^0$ cells are used directly in fusion experiments. More recently, cells of interest have been fused to a mitochondrially depleted cell line. These cybrids were then enucleated and the cytoplasts electrofused to mitochondrially depleted embryonic stem (ES) cells to construct mice with mixed populations of mitochondrial DNA (heteroplasmy) in order to study debilitating mtDNA mutations and deletions (Inoue et al., 2000; Nat Genet, 26:176-181. Sligh et al., 2000, Proc Natl Acad Sci USA, 97: 14461-14466). However, as far as the inventors are aware, nobody has proposed the use of $mt^0$ or $mtDNA^0$ cells to generate clones having true genetic identity.

The construction of embryos generated from $mt^0$ or $mtDNA^0$ donor cells ensures that only one functional population of mtDNA is transmitted to the offspring. This is particularly important as it ensures that the offspring are all truly genetically identical to each other in both nuclear and mitochondrial DNA. Consequently, these genetically identical offspring can be used to study disease and for drug screening since any variation that may be introduced, for example a mutation in a nuclear encoded gene which gives rise to a particular disease, will not be competing against other variables.

If the original $mtDNA^0$ or $mt^0$ cells are used as nuclear donors and fused with cells from the first generation of offspring, members of the second generation of offspring are genetically identical to their parental lineage as well as to each other. This also maintains the strict maternal inheritance of mtDNA and ensures that the tight genetic bottleneck regulating mtDNA transmission is further maintained.

According to a second aspect of the present invention there is provided a method of producing a cloned embryo comprising the steps of (i) introducing genetic material comprising at least genomic DNA from a donor cell into an enucleated recipient cell whereby to form a hybrid cell, (ii) introducing sperm mitochondria into said recipient cell or said hybrid cell, and (iii) causing said hybrid cell to divide to become an embryo.

It is known that following fertilisation, sperm mtDNA persists during embryo development. Observations by the inventors suggest that this sperm mtDNA is isolated to specific embryonic cells. It is thought that these cells eventually become extra-embryonic tissue, such as the placental tissue, since sperm mtDNA has been identified in the placentae of rhesus monkey offspring generated through artificial insemination.

Furthermore it is thought that the presence of sperm mitochondria in the embryo promotes normal development of the organism. It is therefore suggested by the inventors that the supplementing of cloned embryos with sperm mitochondria may assist in the successful development of the clone, irrespective of the method used to produce the clone.

Steps (i) and (ii) may be performed concurrently or step (ii) may be effected before or after step (i). It will be understood that when step (ii) precedes step (i), sperm mitochondria is introduced into the recipient cell, and when step (i) precedes step (ii), sperm mitochondria is introduced into the hybrid cell.

Preferably, step (ii) is undertaken prior to said hybrid cell dividing to form an embryo.

Preferably, step (ii) is effected by introducing sperm mid pieces and tails.

Preferably, said method includes an initial step of mitochondrially depleting said donor cell such that the hybrid cell produced has a single functional mitochondrial population.

According to the second aspect, there is also provided a cloned embryo producible by the method and an animal developed from said cloned embryo.

According to a third aspect of the present invention there is provided a method of producing a hybrid cell from a non-differentiated stem cell, said method comprising the step of (i) introducing cytoplasm from a donor oocyte into an undifferentiated stem cell, whereby to cause said undifferentiated stem cell to behave as a recently fertilised oocyte.

It is known that the co-transplantation of sperm and oocyte cytoplasm into a deficient oocyte results in the onset of fertilisation. Consequently, the inventors postulate that the introduction of donor oocyte cytoplasm into a stem cell will reprogram the cell's components so that the hybrid cell behaves as a recently fertilised oocyte.

Preferably, the method includes the initial step of mitochondrially depleting the stem cell.

Preferably, said method includes the further step (ii) of introducing sperm mitochondria into the stem cell at the same time as, or prior to step (i). Alternatively step (ii) is effected after step (i), i.e. said sperm mitochondria are introduced into said hybrid cell.

Preferably, step (ii) is effected by introducing sperm mid pieces and tails.

According to the third aspect, there is also provided a hybrid cell and an animal producible by the method.

According to a fourth aspect of the present invention there is provided a method of increasing the viability of an oocyte, a zygote or an embryonic cell, including an androgenone or a gynogenone, having abnormally low numbers of mitochondria, said method comprising the step of introducing at least genomic DNA and cytoplasm from an oocyte, a zygote or an embryonic cell, including an androgenone or a gynogenone, having abnormally low numbers of mitochondria into a recipient undifferentiated stem cell from which the genomic DNA has been removed.

It will be understood from the foregoing that the addition of cytoplasm from the oocyte, zygote or the embryonic cell, including an androgenone or a gynogenone, may result in reprogramming of the stem cell causing it to behave as a recently fertilised oocyte.

Preferably, said method further includes a step of introducing sperm mitochondria into said recipient cell. Said sperm mitochondria are preferably introduced into said recipient cell at the same time as, or shortly after the introduction of the embryonic genomic DNA and cytoplasm.

One application of this method is to increase the viability of embryos from females suffering from female factor infertility. This disorder results in non-viable embryos due to improper embryonic development due to incorrect segregation of the mitochondria at cell division, leading to mitochondrial depletion of the embryonic cells. It is suggested that the reprogramming effect of introducing embryonic material (at least genomic DNA and cytoplasm) into the undifferentiated stem cell leading to it acting as a fertilised oocyte will overcome this mitochondria associated problem.

Also according to the fourth aspect there is provided an animal produced from said embryonic cell.

Embodiments of the invention will now be described by way of example only.

The process of embryo reconstruction and production of viable offspring by nuclear transfer is a multistep procedure; each of these will now be described in more detail.

The Recipient Cell.

Oocytes, fertilised zygotes and two cell embryos have all been used as recipient cells for nuclear transfer (NT). In general, oocytes (also termed unfertilised eggs) arrested at metaphase of the second meiotic division have become the recipient of choice. At this point in oocyte development, the genetic material is arranged upon the meiotic spindle and is easily removed using mechanical means. Several reports have demonstrated that during maturation i.e. between the germinal vesicle stage (prophase of the first meiotic division) and arrest at metaphase of the second meiotic division, genomic DNA can be removed and the cell minus its genomic DNA used for NT (Kato Y. Tsunoda Y, Mol Reprod Dev, 1993, 36:2 276-8). The use of fertilised zygotes as recipients has been reported in mouse (Kwon O Y, Kono T, Proc Natl Acad Sci USA, 1996, Nov 12, 93:23 13010-3), cattle (Prather R S, First N L, J Reprod Fertil Suppl, 1990, 41), and pigs (Prather et al., Biol Reprod, 1989, September, 41:3 414-8). In cattle and pigs development of embryos reconstructed using zygotes as recipients is low and on the whole restricted to the exchange of pronuclei. Nuclei or cells of any cell cycle stage may be used as donors of genetic material, however, the cell cycle stage of the recipient must be controlled accordingly.

Preparation of a Recipient by Removal of the Genomic Genetic Material.

This process has in general been termed enucleation, although this is a misleading description as in the majority of recipients used, the genomic DNA is not enclosed within a nuclear membrane at the time of removal (as used herein enucleation should therefore be construed in the general sense of meaning removal of genomic DNA). Removal of the genetic material is possible by physical and or chemical means. In the early reports of nuclear transfer, MII oocytes were simply cut in half on the basis that one half would contain the genetic material and the other would not. Modifications to this approach have been made in order to reduce the volume of cytoplasm, which was removed. This may be achieved by aspiration of a small amount of cytoplasm from directly beneath the $1^{st}$ polar body using glass micropipettes or by using a knife to cut away that part of the oocyte beneath the polar body. To facilitate plasticity of the oocyte it may be pre-treated with the microtubule inhibitor Cytochalasin B or other such agent that disrupts the cytoskeleton. In contrast to physical enucleation, chemical treatment has been demonstrated to cause complete removal of the genetic material in the mouse. Treatment of maturing oocytes with the Topoisomerase inhibitor ectoposide results in the expulsion of all genomic material with the $1^{st}$ polar body (Elsheikh A S, et al, Jpn J Vet Res, 1998, February, 45:4 217-20), however no development to term has been described using recipients produced by this method and there are no reports of this procedure in other species. Centrifugation of MII oocytes combined with Cytochalasin B treatment has been reported to cause enucleation in hamster and cattle oocytes (Tatham et al, Hum Reprod, 1996, July, 11:7 1499-503). The development of embryos reconstructed from such recipients has been reported in cattle but the frequency of development is low.

When using zygotes, the genetic material may be removed by mechanical aspiration of both pronuclei. Dependent upon species, in order to facilitate visualisation of the pronuclei, the zygotes may be centrifuged prior to enucleation.

Introduction of Genetic Material (Embryo Reconstruction).

Having prepared a suitable recipient cell, the donor genetic material must be introduced. Various techniques have been reported including;
1. Cell fusion induced by chemical, viral or electrical means,
2. injection of an intact cell by any method,
3. injection of a lysed or damaged cell by any method,
4. injection of a nucleus by any method.

Any of these methods may be used in any species with some modifications of individual protocols.

Activation of the Reconstructed Embryo.

In addition to the transfer of donor genetic material from the donor cell to the recipient cell, the recipient cell or resultant hybrid cell must be stimulated to initiate development. When using a fertilised zygote as the recipient cell, development has already been initiated by sperm entry at fertilisation. When using MII oocytes as recipients the oocyte must be activated by other stimuli. Various treatments have been reported to induce oocyte activation and promote early embryonic development including; application of a DC electric stimulus, treatment with ethanol, ionomycin, Inositol trisphosphate ($IP_3$), calcium ionophore A23187, treatment with extracts of sperm and treatments which induce calcium entry into the oocyte or which induce release of internal calcium stores. Any of these treatments alone or in combination may be used in the context of the present invention. In addition, such treatments may be combined with inhibitors of protein synthesis (i.e. cycloheximide or puromycin) or inhibitors of serine threonine protein kinases (i.e. 6-DMAP).

Culture of Reconstructed Embryos.

Nuclear transfer reconstructed embryos may be cultured in vitro to a stage suitable for transfer to a final recipient using any suitable culture medium or culture process. Alternatively, embryos may be cultured in vivo in the ligated oviduct of a suitable host animal until a stage suitable for transfer to a final surrogate recipient is reached. Embryos from cattle, sheep and other species may be cultured in a trans-species recipient; e.g. a sheep provides a suitable recipient for bovine, ovine and porcine species. In order to prevent mechanical damage or attack by macrophages to the reconstructed embryos whilst in the oviduct of the temporary recipient, it is usual, but not essential, to embed the embryos in a protective layer of agar or similar material. Alternatively reconstructed embryos may be cultured to term by immediate transfer to a suitable surrogate.

The Development of $mtDNA^0$ Cell Lines from Somatic and Embryonic Stem (ES) Cells Suitable for NT.

$MtDNA^0$ cell lines have been established for a number of cell types, primarily to investigate the effects of mtDNA mutation and deletion. These cell lines still synthesize and maintain mitochondria and an incomplete ETC due to the large number of nuclear encoded genes that contribute to the organelle. Consequently, these cell lines are maintained in an anaerobic media containing uridine, pyruvate and lactate to support their survival in culture. However, these cell lines tend to be immortalised for long-term viability. Recently, this technology was taken further through the generation of ES cell cybrids to create mouse transmitochondrial disease models. The use of differentiated non-transformed primary cultures or ES cells offers the opportunity of generating $mtDNA^0$ cells that have not been transformed and are thus virus-free.

In order to determine the efficiency of the mtDNA depleted cell lines to transcribe and replicate foreign mtDNA, $mtDNA^0$ cells were hybridised to their original (non-mtDNA depleted) cell line to produce a cybrid which was cultured in the presence of DMEM supplemented with 5% FBS, 100 μg bromodeoxyuridine/ml and 50 μg/ml uridine. Viable cybrids were selected through their transfer from anaerobic to aerobic media (selection media)—DMEM supplemented with 5% dialysed FBS and 100 μg bromodeoxyuridine/ml (see King and Attardi, supra) with those cybrids of sufficient OXPHOS capacity surviving. The generation of cybrids allowed for the transcription and replication efficiency of the $mtDNA^0$ cell lines and their ability to repopulate mtDNA to be assessed. Cell growth was monitored and cell viability and expression of individually encoded mtDNA proteins was assessed.

Generation of Cybrid-NT Embryos to Produce the First Generation of Genetically Identical Offspring.

Embryos were generated by NT as previously described (Campbell et al., 1996, Nature 380:64-66, Wakayama et al., Nature 394:369-373). However, non-immortalised foetal and ES mitochondrially depleted cells were used as the source of nuclear DNA and the enucleated oocytes were selected from the same ovary to ensure true genetic identity. Isolated sperm midpieces and tails were injected into cybrid-NT embryos at the time of reconstruction to ensure correct placental function. Cybrid-NT embryos were cultured in vitro up to the blastocyst stage. Embryos were selected using standard morphological criteria and good quality blastocysts were transferred to surrogate recipients.

To ensure that the cytoplasm interacts with the nucleus following Cybrid-NT, the following assays were performed on those blastocysts not transferred to a surrogate recipient: the clustering of mitochondria was monitored through each stage of development to determine whether the mitochondria were in synchrony with cell division; and analyses of gene expression for inner cell mass and trophoblast differentiation and mtDNA transcriptional regulation were analysed.

Recloning of Offspring to Maintain mtDNA Stability.

Technically, the first generation of offspring consist of hybrids or chimeras, as they possess nuclear DNA from one source and mtDNA from another though they were genetically identical to each other. However, the use of the original mitochondrially depleted cell line with oocytes from the offspring generated a second generation that were identical to their parental lineage and to each other. Again, some embryos were cultured to blastocyst stage and analysed for appropriate gene expression and patterns of mtDNA distribution. Blastocyst stage embryos were transferred to surrogate recipients for development to term.

EXAMPLE 1

Ovine Embryo Reconstruction

1. The Generation of Primary Cultures of MtDNA Depleted Ovine Foetal Fibroblast Populations.

Primary cultures of ovine foetal fibroblasts were isolated from day 30 foetuses as described by Schnieke et al. (1997) (Science 1997; 278: 2130-2133). Isolated cell populations were cultured in Dulbecco's modified Eagle's medium (DMEM)/Ham's F12 (1:1v/v) supplemented with 10% FCS (v/v), 15 mM HEPES, 1.2 g/litre sodium bicarbonate, penicillin and streptomycin, pH7.4. Fibroblasts were depleted of mitochondria or mtDNA according to the protocol of King &

Attardi (supra). Briefly, fibroblasts were cultured in DMEM containing 4500 mg/litre glucose and 1 mM pyruvate and supplemented with 5% FBS (v/v), 100 µg bromodeoxyuridine/ml and 50 µg/ml uridine. Cells were grown in the presence of, for example ethidium bromide or Rhodamine 6-G, in order to isolate cells completely lacking mtDNA or having dysfunctional mtDNA or completely lacking mitochondria. After mitochondrial depletion, the cells were maintained in DMEM supplemented with 5% FBS, 100 µg bromodeoxyuridine/ml and 50 µg/ml uridine. In order to determine that the isolated cells are mitochondrially depleted, a batch of the cells were cultured in an aerobic environment, i.e. DMEM supplemented with 5% dialysed FBS and 100 µg bromodeoxyuridine/ml. The absence of a pyrimidine (uridine, in this instance) source in this selection media ensured that those cells unable to generate ATP through OXPHOS would not survive.

2.1. Superstimulation of Donor Ewes and Recovery of Oocytes.

Scottish Blackface ewes were synchronised with progestagen sponges for 14 days (Veramix, Upjohn, UK) and induced to superovulate with single injections of 3.0 mg/day (total 6.0 mg) ovine follicle-stimulating hormone (FSH) (Ovagen, Immuno-chemical Products Ltd. New Zealand) on two successive days. Ovulation was induced with an 8 mg single dose of a gonadotropin-releasing hormone analogue (GnRH Receptal, Hoechst, UK) 24 hours after the second injection of FSH. Unfertilised metaphase II oocytes were recovered by flushing from the oviduct at 24-29 hours after GnRH injection using Dulbecco's phosphate buffered saline containing 1.0% foetal calf serum (FCS) maintained at 37° C. until use.

2.2. Oocyte Manipulation.

Recovered oocytes were maintained at 37° C., washed in PBS 1.0% FCS and transferred to calcium free M2 medium containing 10% Foetal Calf Serum (FCS), at 37° C. To remove the chromosomes (enucleation) oocytes were placed in calcium free M2 containing 10% FCS, 7.5 ug/ml Cytochalasin B (Sigma) and 5.0 ug/ml Hoechst 33342 (Sigma) at 37° C. for 20 minutes. A small amount of cytoplasm from directly beneath the 1st polar body was then aspirated using a 20 µm glass pipette. Enucleation was confirmed by exposing the aspirated portion of cytoplasm to UV light and checking for the presence of a metaphase plate.

3. Embryo Reconstruction.

Groups of 10-20 oocytes were enucleated and placed into 20 µl drops of calcium free M2 medium at 37° C. 5% $CO_2$ under mineral oil (SIGMA). Three protocols were used for embryo reconstruction:—

3.1. "MAGIC" (Metaphase Arrested G1/G0 Accepting Cytoplast).

As soon as possible after enucleation a single $mtDNA^0/mt^0$ cell was placed into contact with the oocyte by using a glass pipette to transfer the cell through the hole previously made in the zona pellucida of the oocyte. The recipient/donor cell couplet was then transferred into a fusion chamber in 200 µl of 0.3M mannitol in distilled water and manually aligned between the electrodes. An AC pulse of 5V was applied for 3 seconds followed by 3 DC pulses of 1.25 kV/cm for 80 µs. The couplets were then washed in calcium free M2, 10% FCS at 37° C. and incubated in the same medium under oil at 37° C. 5% $CO_2$. 30 Minutes prior to activation the couplets were transferred to calcium free M2 medium 10% FCS containing 5 µM Nocodazole. Activation was induced at 32-34 hours post human Chorionic Gonadotropin (hCG) injection. Following activation, the reconstructed zygotes were incubated in medium TC199 containing 10% FCS at 37° C. under 5% $CO_2$ for a further 3 hours. They were then washed 3 times for 5 minutes at 37° C. in the same medium without nocodazole and cultured for a further 12-15 hours prior to transfer to temporary recipient ewes.

3.2. "GOAT" (G0/G1 Activation and Transfer).

At 32-34 hours post hCG injection a single $mtDNA^0/mt^0$ cell was placed into contact with the enucleated oocyte. The couplet was transferred to the fusion chamber in 200 µl of 0.3 M mannitol, 0.1 mM $MgSO_4$, 0.001 mM $CaCl_2$ in distilled water. Fusion and activation were induced by application of an AC pulse of 3V for 5 seconds followed by 3 DC pulses of 1.25 kV/cm for 80 µs. Couplets were then washed in TC199 10% FCS containing 7.5 µg/ml Cytochalasin B and incubated in this medium for 1 hour at 37° C. 5% $CO_2$. Couplets were then washed in TC199 10% FCS and cultured for a further 12-15 hours in TC199 10% FCS at 37° C. 5% $CO_2$.

3.3. "UNIVERSAL RECIPIENT".

Enucleated oocytes were activated 32-34 hours post hCG injection and then cultured in TC199 10% FCS at 37° C. 5% $CO_2$ for 4-6 hours. For activation, oocytes were placed between two parallel electrodes in 200 µl of 0.3 M mannitol, 0.1 mM $MgSO_4$, 0.001 mM $CaCl_2$ in distilled water. Activation was induced by application of 1 DC pulse of 1.25 kV/cm for 80 µs. A single $mtDNA^0/mt^0$ cell was then placed into contact with the oocyte and fusion induced. For fusion the contact surface between the enucleated oocyte and the cell was arranged parallel to the electrodes of the fusion chamber and fusion induced by application of an AC current of 3V for 5 seconds followed by 3 DC pulses of 1.25 kV/cm for 80 µs. The couplets were then incubated in TC199 10% FCS 7.5 µg cytochalasin B for 1 hour at 37° C. 5% $CO_2$. Couplets were then washed and cultured in TC199 10% FCS at 37° C. 5% $CO_2$ for a further 8-11 hours.

4. Embryo Culture and Assessment (All Groups)

After the culture period, fused couplets were double embedded in 1% and 1.2% agar (DIFCO) in PBS and transferred to the ligated oviduct of unsynchronised ewes. After 6 days, recipient ewes were sacrificed and the embryos retrieved by flushing from the oviduct using PBS 10% FCS. Embryos were dissected from the agar chips using 2 needles and development assessed by microscopy. All embryos which had developed to the morula/blastocyst stage were transferred as soon as possible to the uterine horn of synchronised final recipient ewes.

EXAMPLE 2

Bovine Embryo Reconstruction

1. The Generation of Primary Cultures of mtDNA Depleted Bovine Foetal Fibroblast Populations.

The method used corresponds to that described above for Example 1.

2.1. In Vitro Oocyte Maturation.

Ovaries were obtained from a local abattoir and maintained at 28-32° C. during transport to the laboratory. Cumulus oocyte complexes (COC's) were aspirated from follicles 3-10 mm in diameter using a hypodermic needle (1.2 mm internal diameter) and placed into sterile plastic universal containers.

The universal containers were placed into a warmed chamber (35° C.) and the follicular material allowed to settle for 10-15 minutes before pouring off three-quarters of the supernatant. The remaining follicular material was diluted with an equal volume of dissection medium (TCM 199 with Earles salts (Gibco), 75.0 mg/l kanamycin, 30.0 mM Hepes, pH7.4, osmolarity 280 mOsmols/Kg $H_2O$) supplemented with 10% bovine serum, transferred into an 85 mm petri dish and searched for COC's under a dissecting microscope. Complexes with at least 2-3 compact layers of cumulus cells were selected, washed three times in dissection medium and transferred into maturation medium (TC medium 199 with Earles salts (Gibco), 75 mg/l kanamycin, 30.0 mM Hepes, 7.69 mM $NaHCO_3$, pH7.8, osmolarity 280 mOsmols/Kg $H_2O$) supplemented with 10% bovine serum and $1 \times 10^6$ granulosa cells/ml and cultured until required on a rocking table at 39° C. in an atmosphere of 5% $CO_2$ in air.

2.2. Oocyte Manipulation.

Matured oocytes were stripped of cumulus cells 18 hours after the onset of maturation. Denuded oocytes were then washed in calcium free M2 medium containing 10% FCS and maintained in this medium at 37° C. To remove the chromosomes (enucleation), oocytes were placed in calcium free M2 containing 10% FCS, 7.5 ug/ml Cytochalasin B (Sigma) and 5.0 ug/ml Hoechst 33342 (Sigma) at 37° C. for 20 minutes. A small amount of cytoplasm from directly beneath the 1st polar body was then aspirated using a 20 μm glass pipette. Enucleation was confirmed by exposing the aspirated portion of cytoplasm to UV light and checking for the presence of a metaphase plate. Enucleated oocytes were then used for each of the three methods of reconstruction as detailed below.

3. Embryo Reconstruction.

3.1. "MAGIC" (Metaphase Arrested G1/G0 Accepting Cytoplast).

The method used corresponds to that described above for Example 1, except that during fusion the AC pulse was 3V for 5 seconds.

3.2. "GOAT" (G0/G1 Activation and Transfer).

Enucleated oocytes were returned to the maturation medium. At 30 or 42 hours post onset of maturation (hpm) a single $mtDNA^0/mt^0$ cell was placed into contact with the enucleated oocyte. The couplet was transferred to the fusion chamber in 200 μl of 0.3 M mannitol, 0.1 mM $MgSO_4$, 0.001 mM $CaCl_2$ in distilled water. Fusion and activation were induced by application of an AC pulse of 3V for 5 seconds followed by 3 DC pulses of 1.25 kV/Cm for 80 μs. Couplets were then washed in TC199 10% FCS and incubated at 37° C. 5% $CO_2$ for 15-20 hours (30 hpm group) or 4-8 hours (42 hpm group).

3.3. "UNIVERSAL RECIPIENT".

Enucleated oocytes were activated, under the same conditions as described for Example 1, 30 or 42 hours post onset of maturation and then cultured in TC199 10% FCS at 37° C. 5% $CO_2$ for 8-10 hours (30 hpm group) or 4-6 hours (42 hpm group). Contact and fusion were also carried out under the same conditions described for Example 1. The couplets were then cultured in TC199 10% FCS at 37° C. 5% $CO_2$ for a further 12-16 hours (30 hpm group) or 4-6 hours (42 hpm group).

Embryo culture and assessment (all groups) was as described for Example 1.

EXAMPLE 3

Porcine Embryo Reconstruction (Two Stage Nuclear Transfer)

1. The Generation of Primary Cultures of mtDNA Depleted Porcine Foetal Fibroblast Populations.

The method used corresponds to that described above for Example 1.

2.1. Synchronisation Procedure for the Collection of In Vivo Matured Porcine Oocytes.

Altrenogest (Regu-Mate, 18 mg/day, 9AM) was fed for 5-9 days, starting on day 12-16 of the cycle (day 0 is heat). (If no heats are available, Altrenogest should be fed for 14 days.) Gilts were injected with Estrumate (IM, 1.0 ml, 9 AM) during the last Alternogest feeding, and eCG (Equine Chorionic Gonadotropin, 1500 IU IM) injected 14 hrs (11 PM) after the last Altrenogest feeding. hCG (human Chorionic Gonadotropin, 1000 IU, IM) was then injected 80 hrs after the eCG injection (7 AM), with oocytes collected 50 hrs after the hCG injection (9 AM).

3.1. "MAGIC" (Metaphase Arrested G1/G0 Accepting Cytoplast).

Enucleated oocytes were maintained in calcium free medium 10% FCS at 39° C. In the $1^{st}$ stage nuclear transfer it is presently preferred, but not essential, that the donor genetic material is introduced into the enucleated oocyte by piezo aided injection. To aid injection the cytoplast recipients were centrifuged at 13,000×G for 5 minutes. The donor cell was placed into medium containing 12% Polyvinyl Pyrollidone, the cell drawn into the injection pipette and then injected into the oocyte. The cell membrane may be intentionally damaged by selection of an appropriately sized pipette and/or the application of a burst of piezo vibration and repeated pipetting.

The size of the injection pipette is dependent upon the size of the cell. Alternatively, transfer of the nucleus may be achieved by cell fusion. As soon as possible after enucleation a single $mtDNA^0/mt^0$ cell was placed into contact with the oocyte by using a glass pipette to transfer the cell through the hole previously made in the zona pellucida. The cytoplast/cell couplet was then transferred into fusion medium (0.3 M D-Sorbitol supplemented with 0.1 mM $MgSO_4$ & 0.05 mM $CaCl_2$ in $H_2O$, osmolarity 280 mOsM) in the fusion chamber. The couplet was manually aligned between the electrodes. Fusion was induced by application of two DC pulses of 1 kV/cm for 60 μs at intervals of 5s. The couplets were then washed in calcium free medium supplemented with 10% FCS at 37° C. and incubated in the same medium under oil at 37° C. 5% $CO_2$. 30 Minutes prior to activation the couplets were transferred to calcium free medium 10% FCS containing 5 μM Nocodazole. Activation was induced as described for Example 1 above. Following activation, the reconstructed zygotes were incubated in medium NCSU23, 10% FCS at 37° C. 5% $CO_2$ for a further 3 hours. They were then washed 3 times for 5 minutes at 37° C. in the same medium without nocodazole and cultured for a further period of time sufficient for the formation of a pronucleus prior to being used as nuclear donors for the second stage nuclear transfer embryo reconstruction.

3.2. "GOAT" (G0/G1 Activation and Transfer).

Enucleated oocytes were returned to the maturation medium. At 30 or 42 hours post onset of maturation a single mtDNA⁰/mt⁰ cell was placed into contact with the enucleated oocyte. The couplet was transferred to the fusion chamber in fusion medium 0.3 M D-Sorbitol supplemented with 0.1 mM $MgSO_4$ and 0.05 mM $CaCl_2$ in $H_2O$, osmolarity 280 mOsM. Fusion and activation were induced by application of two DC pulses of 1 kV/cm for 60 μsec at intervals of 5 sec. Couplets were then washed in NCSU23 10% FCS and incubated at 37° C. 5% $CO_2$ for a further period of time sufficient for the formation of a pronucleus prior to being used as nuclear donors for the second stage nuclear transfer embryo reconstruction.

3.3. "UNIVERSAL RECIPIENT".

Enucleated oocytes were activated as described for Example 1 and cultured in NCSU23, 10% FCS at 37° C. 5% $CO_2$. After the decay of MPF activity, a single mtDNA⁰/mt⁰ cell was then placed into contact with the oocyte and fusion induced as described above in section 3.2. The couplets were then cultured in NCSU23 10% FCS at 37° C. 5% $CO_2$ for a further period of time sufficient for the formation of a pronucleus, prior to being used as nuclear donors for the second stage nuclear transfer embryo reconstruction.

It will be understood that regardless of the nuclear transfer protocol used (section 3.1, 3.2 or 3.3) the donor nucleus may be transferred by either manual or piezo aided injection. Other chemical or physical means of producing cell fusion may also be employed.

4. Preparation of a Cytoplast for the Second Nuclear Transfer Embryo Reconstruction.

A suitable cytoplast was prepared by activation of an enucleated oocyte as described under 3.3 above. Alternatively, as is preferred at present, a cytoplast was prepared from any in vivo or in vitro produced zygote. After pronuclear formation the zygote was centrifuged, in a suitable buffered medium, at 13,000×g for 5 minutes. This aids visualisation of the pronuclei but is not essential. The centrifuged zygotes were placed into the manipulation chamber in a suitable medium and a portion of cytoplasm containing the two pronuclei was aspirated using a micropipette.

5. Second Stage Nuclear Transfer Embryo Reconstruction.

5.1 Synchronisation Procedure for the Collection of In Vivo Fertilised 1-Cell Porcine Zygotes.

Altrenogest (Regu-Mate, 18 mg/day, 9 AM) was fed for 5-9 days, starting on day 12-16 of the cycle (day 0 is heat). (If no heats are available, feed Altrenogest for 14 days.) Gilts were then injected with Estrumate (IM, 1.0 ml, 9 AM) during the last Alternogest feeding, and eCG (Equine Chorionic Gonadotropin, 1500 IU IM) 14 hrs (11 PM) after the last Altrenogest feeding. Subsequently hCG (human Chorionic Gonadotropin, 1000 IU, IM) was injected 79 hrs after the eCG injection (6 AM). The Gilts were artificially inseminated 24 and 36 hrs after the hCG injection, and embryos collected 50 hrs after the hCG injection (noon).

5.2. Reconstruction of the $2^{nd}$ Stage Nuclear Transfer Embryo.

The donor formed by aspiration of the pronucleus surrounded by a portion of cytoplasm and membrane bound from the $1^{st}$ nuclear transfer embryo was placed below the zona pellucida of the $2^{nd}$ recipient in contact with the recipient. Fusion of the donor and recipient was carried out as in the first stage. In an alternative embodiment, the donor, the pronucleus or the pronucleus surrounded by a portion of cytoplasm was injected into the $2^{nd}$ nuclear transfer embryo.

5.3. Culture of Reconstructed Embryos.

If required, reconstructed embryos may be cultured in vitro using any suitable culture medium and conditions e.g. NCSU medium supplemented with 10% FCS 37° C. in a humidified atmosphere of 5.0% $CO_2$. However, the reconstructed embryos produced above were transferred directly to a synchronised final recipient for development to term.

EXAMPLE 4

Ovine Embryo Reconstruction and Development

1. The Generation of Primary Cultures of MtDNA Depleted Ovine Foetal Fibroblast Populations.

The method used corresponds to that described above for Example 1

2.1. In Vitro Oocyte Maturation

Ovine ovaries were transported from a local abattoir to the laboratory in PBS at 30-32° C. Cumulus-oocyte complexes (COCs) were recovered by aspiration of 2-6 mm follicles using a 21-gauge needle and a syringe and transferred into Hepes-buffered Tissue Culture Medium 199 (TCM 199; Gibco BRL Life Technologies, Pisley, UK) supplemented with 10% foetal bovine serum (FBS, Gibco BRL Life Technologies). Before in vitro maturation, COCs were assessed morphologically and only those that possessed at least three layers of cumulus cells and with a homogenous cytoplasm were selected. Selected COCs were washed three times in maturation medium (bicarbonate-buffered TCM-199 with Earle's salts supplemented with 10% FBS, 5 μg/ml FSH (Foltropin; Vetropharm, Ireland), 5 μg/ml LH (Lutrophin; Vetropharm, Ireland), 1 μg/ml estradiol (Sigma), 0.3 mM sodium pyruvate and 100 μM cysteamine) before incubation in 500 μl droplets of maturation medium (40-50 oocytes/droplet) covered with mineral oil in 4-well dishes (Nunc, Roskilde, Denmark) at 39° C. in 5% $CO_2$ and humidified air for 16-17 h.

2.2. Oocyte Manipulation

After maturation, COCs were treated with 300 IU/ml hyaluronidase (type IV-S; Sigma) and the cumulus cells were removed by vortexing for 2-3 min. The oocytes were stained in Hepes-buffered synthetic oviduct fluid (HSOF) containing 4 mg/ml BSA and 5 μg/ml Hoechst 33342 (Sigma) for 10-15 min. Matured oocytes were enucleated by aspirating anaphase or telophase plates in a small amount of surrounding cytoplasm with a 20 μm glass pipette in manipulation medium (HSOF plus 4 mg/ml BSA and 7.5 μg/ml cytochalasin B). Confirmation of successful enucleation was achieved by visualizing the karyoplast, whilst still inside the pipette, under ultraviolet light. In this manner, the oocyte was not exposed to ultraviolet light. Following enucleation, the resulting cytoplasts were washed extensively in fresh HSOF containing 4 mg/ml BSA and cultured in maturation medium until injection of donor cells.

3. Embryo Reconstruction.

3.1. Nuclear Transfer and Reactivation

The donor cells used for nuclear transfer were induced into a period of confluence (presumptive G0 or G1). One day after routine passage, the culture medium was aspirated and the cells washed three times with fresh changes of PBS. The cells were returned to culture for a further 4-12 days before use. Immediately before injection, a single cell suspension of the donor cells was prepared by standard trypsinization. The cells were pelleted and resuspended in HSOF containing 4 mg/ml BSA and retained in this medium until injection.

A 20 μm pipette was introduced through the same slit in the zona pellucida of the recipient oocyte as made during enucleation and the donor cell placed between the zona and the cytoplast membrane to facilitate close membrane contact for subsequent fusion. Following donor cell injection, the reconstructed embryos were transferred in HSOF containing 4 mg/ml BSA for 5 min until fusion. Reconstructed embryos were washed in fusion buffer (0.3M mannitol, 0.05 mM $CaCl_2$, 0.1 mM $MgSO_4.7H_2O$, 0.5 mM Hepes and 0.05% BSA) prior to fusion. Fusion was performed at room temperature in a fusion chamber having two stainless steel electrodes 200 μm apart overlaid with fusion buffer. The reconstructed embryos were manually aligned between the electrodes, and cell fusion induced with one DC pulse of 40V/cm for 20 μs (Eppendorf Mutiporator). Fusion was determined by microscopic examination before in vitro culture. Reconstructed embryos were activated in HSOF plus 5 μg/ml calcium ionophore (Sigma) for 5 min and cultured subsequently in SOF with 10 μg/ml of cycloheximide and 7.5 μg/ml cytochalasin B for 5 hours at 39° C.

4. Culture of Nuclear Transfer Embryos In Vitro

After chemical activation, the nuclear transfer embryos were placed in 50 μl microdrops of SOFaaBSA medium and incubated under humidified 5% $CO_2$, 5% $O_2$ and 90% $N_2$ gas mix at 39° C. On day three of culture, 5% FBS was added to the medium. On day 6-7, blastocysts development was recorded and is shown in Table 1 below.

TABLE 1

Development In Vitro of Nuclear Transfer Embryos derived from treated and untreated primary ovine foetal fibroblast cells

| Group | Oocytes | Fused (%) | Cleaved (%) | Blastocyst (%) | Cell No. |
|---|---|---|---|---|---|
| Treated foetal fibroblasts | 130 | 95 (73.1%)[a] | 77 (59.2%)[a] | 30 (23.1%) | 74.5 |
| Control untreated foetal fibroblasts | 134 | 116 (86.6%)[b] | 108 (80.6%)[b] | 43 (32.1%) | 94.3 |

[a,b]different superscripts within a column differ significantly (P < 0.05).

General Methodology.

The Monitoring of Cybrid-NT Embryonic Development Mitochondrial Synchrony.

The clustering of mitochondria was monitored through each stage of development to determine whether the mitochondria were in synchrony with cell division. Mitochondria were stained using, for example, MitoTracker (Molecular Probes, Eugene, Oreg.) or JC-1 (Molecular Probes, Eugene, Oreg.) and embryos were examined using a Leica TCS SP2 multiphoton confocal microscope as described by Bavister et al. (Hum Reprod 2000; 15 Suppl 2;189-198).

Evaluation of Cybrid-NT Embryonic Gene Expression for:

i) Inner Cell Mass and Trophoblast Differentiation:

Individual blastomeres, developed to different stages of embryonic development by Cybrid-NT and IVF were prepared by treating whole embryos with pronase to remove the zona pellucida and then with calcium free medium to separate individual blastomeres. Each blastomere was screened for molecular markers associated with cell differentiation. For example, Mash-2 and gcm-1 have been identified with trophectoderm differentiation, Pax genes and neurogenic basic helix-loop-helix (bHLH) transcription factors with neuronal tissue and the transcription factor OCT-4 with pluripotent stem cell development. Total RNA was isolated and gene expression screened by Real-Time RT-PCR.

ii) MtDNA Transcriptional Regulation:

Mitochondrial transcription factor A (mtTFA) is a transcriptional accessory protein and is putatively the major regulator of the number of mtDNA transcripts. MtTFA is vital to embryo survival particularly during development and differentiation. MtTFA expression was screened to determine whether embryonic mtDNA transcription and replication were triggered as anticipated (Piko & Taylor, 1987, Dev Biol, 123: 364-374) using RT-PCR. Furthermore, individual blastomeres were analysed to determine whether patterns of mtDNA distribution were uniform or whether uneven segregation appeared early on. MtDNA copy number was assessed using Real Time PCR as described by Reynier et al. 2001 (Mol Hum Reprod; 7: 425-429). The expression of further gene products, such as Nuclear Respiratory Factor 1 (NRF1), can be screened to determine if mitochondrial transcription and replication proceed as expected. In the embryo, expression of NRF1 is thought to occur prior to mtTFA expression (Huo & Scarpulla, (2001), Mol. Cell Biol., 21: 644-54

Confirmation of the Presence and Origin of MtDNA in Cybrids, Embryos, Foetuses and Offspring.

Amongst other assays, Allele Specific (AS)-PCR, SNPs, AS-Real Time PCR and RFLP PCR were performed to determine the presence of and origin of mtDNA in the samples analysed.

Isolation of Sperm Midpieces and Tails for use with Reconstructed Embryos.

Sperm heads and tails (including the midpiece containing the mitochondria) were partially drawn into the micropipette until the neck was against the rim. Piezo pulses were then applied until the axoneme was ruptured. Isolated midpieces and tails were injected into cybrid-NT embryos at the time of reconstruction (concomitantly whilst using Piezo assisted nuclear injection) or immediately following reconstruction (for example, ovine embryos are reconstructed by cell fusion and then injected with the mitochondrial fraction).

Assessment of Mitochondrial Function in MtDNA Depleted Cells Mitochondrial Membrane Potential ($\Delta\psi_m$):

MtDNA⁰ cells were prepared for flow cytometric analysis of $\Delta\psi_m$ using an established mitochondrial membrane potential marker, such as JC-1 (Molecular Probes, Eugene, Oreg.) and observed under a fluorescent microscope. Cell viability was substantiated by treating the cells with a viability stain, such as the LIVE DEAD™ stain (Molecular Probes, Eugene, Oreg.).

Assessment of the Specific Proteins Encoded by the Mitochondrial Genome.

To determine whether mtDNA depletion was effective and that mtDNA had repopulated mtDNA⁰ cells, immunocytochemistry (ICC) was performed using antibodies specific to some of the subunits encoded by mtDNA, for example subunits I and II of Complex IV (cytochrome c oxidase—COX) of the electron transport chain. In mtDNA-depleted cells, a fluorescent signal was not observed whilst repopulated cells fluoresced. Furthermore, ICC on subunits IV, Va and VIc of Complex IV, which are encoded by nuclear DNA confirms that the mitochondria possess the nuclear encoded proteins. ICC was supported by Western Blotting and densitometric quantification was performed in this respect. These assays were also performed on positive controls, i.e. known cell types possessing mtDNA and previously repopulated mtDNA⁰ cells; and negative (other mtDNA⁰ cell lines) controls.

Immunocytochemistry (ICC).

Cybrids were grown on coverslips in 6-well dishes in DMEM supplemented with 5% dialysed FBS and 100 μg bromodeoxyuridine/ml at 37° C. in 5% $CO_2$ and mt⁰ cells in anaerobic media as described above. Coverslips were rinsed in PBS and fixed for 30 minutes in 4% paraformaldehyde in PBS containing 0.1% Triton-X 100, pH 7.2. Tissues were preserved on slides. Cells were immunostained using primary monoclonal antibodies specific to the ETC, such as subunits I, II, IV, Va and IVc of cytochrome c oxidase. This was followed by incubation with an appropriate secondary, IgG-FITC antibody. Labelled cells were visualised by fluorescence microscopy and the percentage of positive cells determined after counting 200 cells per slide, with duplicate slides for each primary antibody used. Further negative controls were included with cells being stained as above, but omitting the primary antibody step and incubating with the secondary antibody only.

Western Blotting.

Cells were collected, washed in PBS and pelleted. Cells were lysed by repeated freeze-thaw cycles and soluble protein concentration determined by use of the Bio-Rad protein assay (Bio-Rad). Lysates were boiled after addition of 2× sample buffer and 100 μg total protein was run on a 10% polyacrylamide gel, alongside an appropriate Kilo Dalton ladder, for 45 minutes at 200V. Proteins were blotted onto PVDF membrane (Imobillon) for 1 hour at 400 mA and subsequently blocked in 5% Marvel in PBS plus 0.1% Tween 20 (PBS-T) for 2 hours. After washing in PBS-T, the blot was incubated in primary antibody to the appropriate subunit for one hour at room temperature. After further washing in PBS-T, the blot was incubated in the appropriate secondary antibody (IgG conjugated to horseradish peroxidase (HRP)) for one hour before washing in PBS-T and visualisation of protein bands was through the ECL system (Anachem). Visualised bands were measured by densitometry.

MtDNA Depletion.

ICC was performed with a monoclonal anti-DNA antibody to visualise mtDNA content. Anti-DNA antibodies stain nuclei and cytoplasm. In mtDNA⁰/mt⁰ cells, only nuclei were stained whilst in the cytoplasm no staining was observed. In cybrids, both nuclei and cytoplasm were stained to show the presence of nuclear DNA and mtDNA. Mitochondrial depletion was also supported by Southern blot analysis. Total DNA was extracted from the cells and digested with the restriction enzyme PvuII, electrophoresed through a 0.8% agarose gel, and transferred to nitrocellulose. Filters were hybridised simultaneously with two probes. One probe was the entire human mitochondrial genome (16.6 kb) and the other, for example, was a 5.8 kb EcoRI insert from a cloned fragment containing the nuclear encoded 18S rDNA sequence. Probes were prepared with a random primer labeling kit. Filters were hybridised with the two probes. Final washings were carried out in 1×SCC and 0.1% SDS. Hybridisation and washings were performed at 65° C.

The nitrocellulose filters were scanned using a blot analyser to determine quantities of mtDNA present.

It should be understood that the methods of the present invention are applicable to non-human species and, where the law permits, to humans.

The invention claimed is:

1. An in vitro method of producing a viable hybrid cell having a single functional mitochondrial population, comprising the step of introducing in vitro genomic DNA from a mitochondrially depleted mammalian donor cell into a recipient mammalian cell of the same species from which genomic DNA has been removed, wherein the recipient cell is an oocyte, a zygote, or a cell from a two-cell embryo.

2. The method according to claim 1, wherein the recipient cell is in an arrested state during DNA removal.

3. The method according to claim 2, wherein the recipient cell is an oocyte which is arrested at metaphase of the second meiotic division when the genomic DNA is removed.

4. The method according to claim 2, further comprising the step of reactivation of the recipient cell after the genomic DNA has been removed, and preferably after the introduction of genomic DNA from the donor cell.

* * * * *